United States Patent
Hickey

(10) Patent No.: US 10,724,055 B2
(45) Date of Patent: Jul. 28, 2020

(54) METHODS FOR SUSTAINING THE VIABILITY OF MICROORGANISMS DURING A CESSATION OF SYNGAS FLOW AND PROCESSES FOR STORAGE AND REACTIVATION OF MICROORGANISMS

(71) Applicant: Synata Bio, Inc., Warrenville, IL (US)

(72) Inventor: Robert Hickey, Okemos, MI (US)

(73) Assignee: Synata Bio, Inc., Warrenville, IL (US)

( * ) Notice: Subject to any disclaimer, the term of this patent is extended or adjusted under 35 U.S.C. 154(b) by 23 days.

(21) Appl. No.: 15/744,666

(22) PCT Filed: Jul. 13, 2016

(86) PCT No.: PCT/US2016/042069
§ 371 (c)(1),
(2) Date: Jan. 12, 2018

(87) PCT Pub. No.: WO2017/015022
PCT Pub. Date: Jan. 26, 2017

(65) Prior Publication Data
US 2018/0201957 A1 Jul. 19, 2018

Related U.S. Application Data

(60) Provisional application No. 62/193,942, filed on Jul. 17, 2015.

(51) Int. Cl.
*C12P 7/06* (2006.01)
*C12N 1/20* (2006.01)
*C12N 1/30* (2006.01)

(52) U.S. Cl.
CPC ........... *C12P 7/065* (2013.01); *C12N 1/20* (2013.01); *C12N 1/30* (2013.01); *Y02E 50/17* (2013.01)

(58) Field of Classification Search
None
See application file for complete search history.

(56) References Cited

U.S. PATENT DOCUMENTS

| 9,034,618 B2 * | 5/2015 | Adams | C12N 1/20 435/160 |
| 2014/0051139 A1 * | 2/2014 | Lokken | C12P 7/065 435/140 |
| 2014/0273125 A1 * | 9/2014 | Hickey | C12P 7/16 435/160 |

FOREIGN PATENT DOCUMENTS

| WO | WO 2009/114127 A1 | 9/2009 | |
| WO | WO 2010/098679 A1 | 9/2010 | |
| WO | WO-2010098679 A1 * | 9/2010 | ............... C12N 1/04 |

OTHER PUBLICATIONS

Ramio-Pujol (Impact of formate on the growth and productivity of Clostridium ljungdahlii and Clostridium carboxidivorans P7 grown on syngas, 2014) (Year: 2014).*
Ramio-Pujol et al., "Impact of formate on the growth an productivity of *Clostridium ljungdahlii* PETC and *Clostridium carboxidivorans* P7 grown on syngas," *International Microbiology* 17: 195-204 (2014).
European Patent Office, International Search Report and the Written Opinion in International Application No. PCT/US2016/042069 (dated Oct. 12, 2016).

* cited by examiner

Primary Examiner — Nghi V Nguyen
(74) Attorney, Agent, or Firm — Leydig, Voit & Mayer, Ltd.

(57) ABSTRACT

The methods are disclosed for sustaining a population of microorganisms in an aqueous fermentation broth used in a process to convert syngas to alcohol when the supply of syngas is impaired. The methods involve supplying at least one formate moiety at a rate and amount sufficient to maintain the population of microorganisms. The introduction of the formate moiety also results in the production of at least one metabolic compound other than ethanol and/or acetate by the microorganisms. The metabolic compound can comprise at least one energy storage compound which can be used to support the microorganisms during processing, storage and reactivation.

18 Claims, No Drawings

METHODS FOR SUSTAINING THE VIABILITY OF MICROORGANISMS DURING A CESSATION OF SYNGAS FLOW AND PROCESSES FOR STORAGE AND REACTIVATION OF MICROORGANISMS

CROSS-REFERENCE TO RELATED APPLICATIONS

This patent application is the U.S. national phase of International Application No. PCT/US2016/042069, filed Jul. 13, 2016, which claims the benefit of U.S. Provisional Patent Application No. 62/193,942, filed on Jul. 17, 2015, which are both incorporated by reference in their entireties herein.

BACKGROUND

Anaerobic fermentations of hydrogen and carbon monoxide involve the contact of the substrate gas in an aqueous fermentation menstruum with microorganisms capable of generating alcohols such as ethanol, propanol, i-butanol and n-butanol. The production of these alcohols requires significant amounts of hydrogen and carbon dioxide and/or carbon monoxide. For instance, the theoretical equations for the conversion of carbon monoxide and hydrogen to ethanol are:

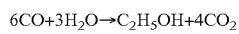

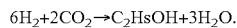

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide and the like.

These anaerobic fermentation processes are suitable for continuous processes. The syngas is passed into a bioreactor containing the aqueous fermentation broth for the bioconversion. Off gases can be removed from the bioreactor, and aqueous broth can be withdrawn from the bioreactor for recovery of the product alcohol at a rate sufficient to maintain steady-state operation. For such processes to be commercially viable they must be able to benefit from the advantages of scale, and thus facilities using these processes need to be able to produce upwards of 50 or 100 million or more gallons of product alcohol per year. These anaerobic fermentation processes necessarily involve the mass transfer of substrate from the gas phase into the liquid phase for access by the microorganisms. These mass transfer considerations together with economies of scale, tend to favor the use of large reactors for commercial-scale facilities. Hence, commercial scale reactors, i.e., those with liquid capacities of at least 1 million, and more often at least about 5, say, 5 to 25, million, liters would be advantageous.

The start-up of these commercial-scale facilities can be problematic due to the large volume of microorganisms required and the time required to grow a sufficient population of the microorganisms. The microorganisms for the anaerobic fermentation typically are expected to be generated by seed farms at the site of the facility. The capital and operating expense for a seed farm is not insignificant. Usually the seed farms are comprised of a sequential series of reactors of increasing size with the final reactor having enough volume to provide an initial charge to the commercial-scale reactor. Usually, the growth in each seed farm stage is targeted to increase the size of the population by a factor of 10 and each stage usually takes from 2 to 7 days to achieve the sought growth. Once charged from the seed farm, the reactor is then operated to promote the growth of the population of microorganisms while increasing the volume of the aqueous medium in the reactor until steady-state is achieved. U.S. Published Patent Application 20130078693 discloses processes for starting up and operation of deep tank anaerobic fermentation reactors.

The supply of syngas is subject to disruptions, both planned and unplanned. The microorganisms used for the bioconversion of syngas to alcohol have a limited period where viability can be retained after a cessation of flow of syngas. Under typical temperatures used for the bioconversion, the microorganisms quickly lose viability, and a loss of syngas for even a short period, e.g., as little as 6 to 24 hours, can result in the preponderance, if not substantially all, of the population of microorganisms being killed. Reestablishing the population of microorganisms after such a decrease or cessation of syngas flow requires time, and during this time alcohol is not being produced at the sought rates. Thus, it is important for a commercial-scale facility to be able to substantially maintain the population of microorganisms as viable as possible during any period where the syngas feed is materially decreased or ceased. Any method for maintaining the viability of the population of microorganisms should be effective for at least the most frequent duration of impaired syngas supply, which is typically at least about 6 hours, and more often at least about 12 to 24 hours, and potentially for several days to a week. It is axiomatic that any such method be able to be quickly implemented to minimize loss of viability of the population of microorganisms. Moreover, the method itself should not induce unduly adverse effects on the microorganisms. Further, the method should not unduly hinder resumption of, or otherwise adversely affect, the normal operations once the impairment of the syngas supply has been alleviated, and the method should be economically viable to implement in a commercial-scale facility.

One option is to introduce sugar into the fermentation broth as substrate for the microorganisms in the event of a syngas feed interruption. This option would increase the risk of microbial contamination since it provides an environment conducive to the growth of a wide variety of microorganisms. It also would result in the generation of free (unionized) acid. Thus the addition of alkalinity is required to avoid killing the microorganisms. For instance, one mole of fructose would yield three moles of acetic acid.

Adams, et al., in United States Patent Application Publication 2010/0227377 A1 propose adding carbon dioxide during periods of decrease or ceased syngas flow to a fermentation broth used to produce ethanol. They postulate that carbon dioxide and ethanol serve to provide energy back to the culture to maintain viability. The ethanol is converted to acetic acid and hydrogen. The hydrogen is available for the $H_2/CO_2$ conversion. The method disclosed by Adams, et al., is not without challenges. First, the method requires the availability of carbon dioxide and its introduction into the fermentation reactor. The dissolved concentration is dependent upon the gas transfer rate and uptake by the microorganisms and thus is difficult to control. Second, the metabolic reaction results in the production of acetic acid. This can result in a significant accumulation of free (un-ionized) acids in the fermentation reactor. The acidity must therefore be addressed by the addition of an alkalinity source, but the build-up of the cation associated with the alkalinity source can reach inhibitory levels. Moreover, the patent applicants do not disclose methods for maintaining the redox potential of the fermentation broth suitable for restart of the syngas fermentation once the flow of syngas can be restored.

Accordingly, improved methods are sought to maintain a viable microorganism population in a fermentation broth during periods of syngas feed interruption where the method can be quickly implemented upon the occurrence of the syngas outage, do not rely upon mass transfer of gas into the aqueous broth, are operable in commercial-scale facilities, do not result in undue pH changes or other operational challenges, are tolerant of under and over dosages, do not unduly consume product alcohols, and are economically viable for commercial-scale operations.

In some instances, it is desired to store microorganisms for later use to make alcohols from syngas. Advantageously the microorganisms are provided in a concentrated mass to reduce the volume that needs to be stored or transported. Common practice for storing microorganisms for long periods of time is freeze drying where the metabolic rate of the microorganisms for all practical purposes ceases. The freeze dried microorganisms can then be reactivated in a fermentation broth. Freeze drying and storage, particularly for the large volumes of microorganisms required for a commercial scale reactor, is commercially impractical.

Moreover, the stored microorganisms need to be effectively reactivated when needed. One practice is to supply sugar to the microorganisms being reactivated and then, once metabolic activity of the population of microorganisms is at a desired level, syngas feed is resumed. This practice suffers from the potential that adventitious microorganism populations can also grow on the sugar substrate. Additionally, the sugar reactivation provides a time delay in the ability to use the microorganisms to make product alcohols and introduces a further step in the reactivation procedure.

Processes are sought to obtain microorganisms from the fermentation reactor and store the microorganisms until needed, and to do so in a cost effective manner in which the viability of the microorganisms is retained and in which the processes for obtaining and storing the microorganisms do not cause undue stress on the microorganisms such that mutations or other changes to the microorganisms occur and in which reactivation is facilitated.

SUMMARY

By the methods of this invention the viability of a population of microorganisms being used for the bioconversion of syngas to alcohol can be sustained in the event of a cessation of the supply of syngas (impairment of syngas supply) to the aqueous fermentation broth by supplying to the broth limited, but sufficient, amounts of soluble formate salt or formic acid or both ("formate moiety"), which are relatively inexpensive commodity chemicals and can be easily stored at the site, to substantially maintain the microorganism population. The methods of this invention are particularly useful where the duration of the impairment of syngas supply is anticipated to be relatively short. Nevertheless, more extended impairments in syngas supply can be accommodated. The methods of this invention can also be used to maintain the viability of the population of microorganisms as the fermentation broth is being cooled to temperatures suitable for longer term storage of the microorganisms. The storage of the microorganisms may be retained on site for use in start-up of a bioreactor or transported for use at another site.

In the methods of this invention, it has been found that the addition of a formate moiety results in the generation of carbon dioxide from the broth without either undue buildup of acetate concentration in the broth or significant consumption of product alcohol. The methods of this invention typically do not result the observable evolution of significant amounts of hydrogen from the broth. The absence of hydrogen generation is unexpected as the degradation of formic acid provides one mole of carbon dioxide and one mole of hydrogen per mole of formic acid. Additionally, the evolution of carbon dioxide from the broth is usually only a fraction of the theoretical carbon dioxide equivalents in the introduced formate moiety. The metabolic mechanisms involved in sustaining the population of microorganisms are not fully understood. While not wishing to be limited by theory, it is believed that the microorganisms bioconvert the formate moiety into redox products which are carbon dioxide and one or more reducing equivalents other than hydrogen. The reducing equivalents are believed to be used to make at least one metabolic compound which is other than ethanol and/or acetic acid (herein referred to as "Metabolic Compound"). The Metabolic Compound is believed to be at least one of pyruvate and metabolic derivatives thereof.

It is further observed that the formate moiety at low feed rates is more effective in maintaining the viability of the microorganism population than an electron-equivalent amount of syngas. Again, without wishing to be limited by theory, it is believed that in some instances at least one Metabolic Compound assists in sustaining the microbial population, herein referred to as energy storage compound. In most instances the concentration of product alcohol in the broth is slightly reduced in the practiced methods of this invention; however, the loss of product alcohol is far less than that in the methods disclosed in United States Patent Application Publication 2010/0227377 A1 (Adams, et al.). Hence it is believed that another metabolic mechanism for sustaining the population of microorganisms exists other than the bioconversion of carbon dioxide and ethanol as disclosed by Adams, et al.

If desired, the methods of this invention can be implemented while retaining the aqueous fermentation broth in the bioreactor used for the syngas bioconversion. Advantageously the supply of the formate moiety to the fermentation broth, since the formate moiety is in liquid form, is capable of being controlled with good precision as no gas to liquid mass transfer is involved. Consequently, the rate of addition of formate moiety can be supplied at a controlled rate that provides the sought viability of the microorganism population without exceeding the rate at which the viable microorganism population is capable of bioconverting the formate moiety. Hence, the amount of formate moiety required to sustain the population of microorganisms does not have to be at a level where the aqueous fermentation broth has to contain a substantial formate anion concentration. Moreover, the formate moiety is capable of being quickly dispersed within the aqueous fermentation broth such that the formate moiety is immediately and substantially uniformly available to the microorganisms in even commercial-scale bioreactors. Thus the methods of this invention can be implemented quickly in the event of an impairment or interruption in syngas supply to attenuate loss of viability of the population of microorganisms.

Again, without wishing to be limited by theory, it is believed that the methods of this invention at low levels of formate moiety addition promote microorganisms going into a state where a metabolic shift occurs and there is little to no growth and where the supplied reducing equivalents help the bacteria maintain their membrane potential and other functions to remain viable. Accordingly, the amount of energy required to maintain the population of microorganisms is a portion of that required where the microorganisms are reproducing and are generating alcohols. Unlike some prior processes, the methods of this invention do not generate undue amounts of acid, e.g., acetic acid, requiring neutralization to avoid further impairment of the microorganism population. Thus, the microorganisms are more able to maintain their redox potential and retain viability of other functions. Since the broth can be readily maintained under pH and redox conditions typically used for the anaerobic bioconversion of syngas to alcohol, the methods of this invention generally do not increase the risk of contamination by other microorganisms such as could occur if carbohydrate were used as an energy source for the microorganisms during the impairment of syngas supply. It should be understood that it is not essential for the entire population of microorganisms to survive for a method to sustain the viability of the population of microorganisms. The objective is to maintain sufficient populations of microorganisms such that upon resumption of the syngas feed, full production rates can promptly be achieved through a combination of microorganisms returning from their basal state and population growth. For example, at a population of 25 percent of the sought population, only two doublings of viable microorganisms are required which typically can be accomplished for most microorganisms in less than about 36 hours, and sometimes in less than about 18 hours.

The temperature of the aqueous fermentation broth need not be lowered to maintain the population of microorganisms during a typical, relatively short impairment of syngas supply. This is particularly beneficial in commercial scale bioreactors having large volumes of fermentation broth where rapid cooling is not economically feasible. However, lowering the temperature can result in a further reduction in the metabolic rate of the microorganism. Advantageously, the methods of this invention can provide sufficient time for a commercial-scale bioreactor to be cooled by economically viable unit operations to further reduce the metabolic rate of the microorganisms if an extended impairment in syngas supply is expected. The methods of this invention do not require the presence of any normally gaseous substrate to be added to fermentation broth although substrate gases as well as inert gases, e.g., for agitation and/or purging, can be used.

In one broad aspect, this invention pertains to a method for sustaining a population of microorganisms for the bioconversion of syngas to alcohol in an aqueous fermentation broth in the event of an impairment of syngas supply to the fermentation broth, said method comprising continuously or intermittently adding to the fermentation broth during the period of impaired syngas feed a formate moiety comprising at least one of formate anion and formic acid.

In its broad aspect this invention also pertains to methods for sustaining a population of microorganisms having the Wood-Ljungdahl pathway for the bioconversion of syngas to alcohol contained in an aqueous fermentation broth in the event of a cessation of syngas feed to the fermentation broth being used for the bioconversion which broth contains said alcohol, which methods comprise continuously or intermittently adding during the period of ceased syngas supplying at least one of soluble formate salt and formic acid, to the fermentation broth at a rate sufficient to substantially maintain a microorganism population.

The amount of formate moiety introduced into the fermentation broth can vary over a wide range. Typically, the higher the rate of formate moiety addition, the shorter the duration to resume normal operation subsequent to the impairment of syngas supply. Where relatively short impairments of syngas supply are anticipated, e.g., less than a few hours, a portion of the microorganisms will naturally be able to survive. Hence, the rate of formate moiety addition can be relatively low and yet still enable desirable durations of syngas supply impairment such that normal operations can resume. Within these broad guidelines, the rate of formate moiety supplied during the period of impairment of the syngas supply is generally sufficient to provide at least about 1 or 2 percent of the electrons from the syngas that were being consumed at steady-state prior to the impairment of syngas supply (this relationship is sometimes referred to herein as the Prior Electron Supply Rate). In some instances the benefit of higher rates of supply of formate moiety starts to diminish where the formate moiety provides over about 20 or 25 percent of Prior Electron Supply Rate. Usually, the rate of formate moiety supplied during the period of impairment of the syngas supply is generally sufficient to provide between about 2 to 15 percent of the Prior Electron Supply Rate.

At the conclusion of the duration of decreased or ceased syngas feed, syngas can be introduced into the aqueous fermentation broth under bioconversion conditions. If the temperature of the aqueous fermentation broth was lowered to reduce metabolic activity, the temperature can be increased before or after the initiation of the syngas feed.

In a further aspect, this invention pertains to processes for the storage and reactivation of acetogens for the bioconversion of syngas to product alcohols. The processes of this invention can reduce stress on the microorganisms during formation of microbial, or microorganism, concentrates, storage of the concentrates and reactivation of the microorganisms from the stored microorganism concentrate. The reduced stress can attenuate the risk of losing performance consistency of the microorganism culture. In some instances, the microorganisms can be stored under static conditions at temperatures as high as 10° C. to 20° C., which is in the range of chilling water in many chemical manufacturing facilities.

In its broad aspect, this invention pertains to processes for the storage and reactivation of microorganisms for the bioconversion of syngas to alcohol comprising:

a. continuously or intermittently introducing into a fermentation broth containing said microorganisms at least one formate moiety of the group consisting of soluble formate salt and formic acid under fermentation conditions, preferably comprising a temperature between about 30° C. and 40° C. for mesophilic microorganisms and between about 50° C. to 65° C. for thermophilic microorganisms to produce at least one Metabolic Compound;

b. cooling the microorganisms to a temperature below about 25° C.;

c. storing, preferably statically, said cooled microorganisms at a temperature below about 25° C., preferably between about 10° C. to 20° C. or 25° C.; and d. reactivating the stored microorganisms by warming to a temperature suitable for the bioconversion and subjecting the microorganisms to syngas fermentation conditions including continuously supplying syngas.

The microorganisms may metabolize at least one energy storage compound at least during step (d).

In some instances, the Metabolic Compounds comprise at least one energy storage compound, and most preferably the energy storage compound is associated with the microorganisms. In some instances the microorganisms metabolize said at least one energy storage compound at least during step (d).

Preferably the fermentation broth of step (a) is separated to provide a solids depleted liquor phase and a microorganism concentrate of said microorganisms, and most preferably, the concentrate has said at least one Metabolic Compound associated therewith. Often the microorganism concentrate has a solids content of at least about 30 grams per liter. By the separation, the volume that is to be cooled in step (b) and stored in step (c) is reduced thereby saving energy and storage capacity. The reactivation of step (d) can be of the microorganism concentrate or a fermentation broth into which the microorganism concentrate is introduced. Since the formate moiety reduces the metabolic activity of the microorganisms, the separation and cooling of the microorganisms can occur with minimal adverse effect on the microorganism population.

Step (a) is preferably conducted of a sufficient duration that the addition of external energy source such as sugar, need not be provided. In general, step (a) is conducted for at least about 30 minutes, and sometimes between 1 and 24, say, 2 and 20, hours. In one aspect of the invention, formate moiety is introduced continuously or intermittently during step (d) until the microorganisms are at a desired temperature for syngas conversion.

In one embodiment, the process is for the bioconversion of syngas to alcohol, whereby prior to step (a), the following steps are performed:

introducing syngas into a fermentation broth comprising a population of microorganisms, bio-converting the syngas to alcohol, and reducing or terminating the flow of syngas into the fermentation broth.

The flow or supply of syngas into the fermentation broth may be reduced by at least 10 vol %, preferably at least 20 vol %, for example, at least 40 vol %. In one embodiment, the flow or supply of syngas may be reduced by 50 vol % to 100 vol %, for example, 60 vol % to 100 vol %.

DETAILED DISCUSSION

All patents, published patent applications and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Alcohol means one or more alkanols containing two to six carbon atoms. In some instances the alcohol is a mixture of alkanols produced by the microorganisms contained in the aqueous fermentation broth.

Aqueous broth, or aqueous fermentation broth, means a liquid water phase which may contain dissolved compounds including, but not limited to hydrogen, carbon monoxide, and carbon dioxide. The broth may, but is not required, to contain microorganisms.

A bioreactor assembly is an assembly of one or more vessels suitable to contain aqueous fermentation broth and microorganisms for the bioconversion and can contain associated equipment such as injectors, recycle loops, agitators, and the like.

An energy storage compound is a compound that is produced by a microorganism from a reducing equivalent and can be metabolized by the microorganism in the absence or reduction in availability of substrate. Examples of energy storage compounds include, but are not limited to, pyruvate and derivatives such as polyhydroxyalkanoates, glycogens, lipids such as triglycerides, phospholipids, carbohydrates, and carboxylates.

Intermittently means from time to time and may be at regular or irregular time intervals.

Substantially maintain a population of microorganisms means that at least 25 percent of the microorganisms retain viability.

Syngas means a gas containing at least one of hydrogen and carbon monoxide and may, and usually does, contain carbon dioxide.

Overview

The methods of this invention are used to sustain a population of microorganisms in an aqueous fermentation broth used in a process to convert syngas to alcohol when the supply of syngas is ceased. The methods involve supplying formate moiety at a rate and amount sufficient to maintain the population of microorganisms.

Syngas Bioconversions

Anaerobic fermentation to produce product alcohol uses a substrate (syngas) comprising at least one of (i) carbon monoxide and (ii) carbon dioxide and hydrogen. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas.

Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. These gases may have substantially different compositions than typical syngas, and may be essentially pure hydrogen or essentially pure carbon monoxide. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction.

The alcohol produced by the bioconversion of syngas will depend upon the microorganism or combination of microorganisms used for the fermentation and the conditions of the fermentation. Bioconversions of CO and $H_2/CO_2$ to n-butanol, propanol, ethanol and other alcohols are well known. For example, a concise description of biochemical pathways and energetics of such bioconversions have been summarized by Das, A. and L. G. Ljungdahl, *Electron Transport System in Acetogens* and by Drake, H. L. and K.

Kusel, *Diverse Physiologic Potential of Acetogens*, appearing respectively as Chapters 14 and 13 of Biochemistry and Physiology of Anaerobic Bacteria, L. G. Ljungdahl eds. Springer (2003). Any suitable microorganisms that have the ability to convert the syngas components: CO, $H_2$, $CO_2$ individually or in combination with each other or with other components that are typically present in syngas may be utilized. The microorganisms may be eukaryotes, archaea, or bacteria. In some embodiments, the archaea may be, for example, pyrocochus furiosus. In some embodiments, the bacteria may be Gram negative or Gram positive. In some embodiments, the Gram positive bacteria may be, for example, of the *Clostridium, Bacilli*, or *Erysipelotrichia* genus.

Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Pat. No. 8,143,037.

Pathways for the production of akanols having three carbons include, but are not limited to, *Propionibacterium* species (*Propionibacterium acidipropionici, Propionibacterium acnes, Propionibacterium cyclohexanicum, Propionibacterium freudenreichii, Propionibacterium freudenreichii shermanii, Propionibacterium pentosaecum*) and several other anaerobic bacteria such as *Desulfobulbus propionicus, Pectinatus frisingensis, Pelobacter propionicus, Veillonella, Selenomonas. Fusobacterium, Bacteroides fragile, Prevotella ruminicola, Megasphaera elsdenii, Bacteroides vulgates*, and *Clostridium*, in particular *Clostridium propionicum*.

Mixed cultures of anaerobic microorganisms useful for the bioconversions of syngas to alkanols as has been discussed above. The mixed cultures can be syntrophic and involve C1-fixing microorganisms and microorganisms that bioconvert the products to the C1-fixing microorganisms to higher alkanols. C1-fixing microorganisms include, without limitation, homoacetogens such as *Clostridium ljungdahlii, Clostridium* autoethanogenum, *Clostridium ragsdalei, Clostridium palustris*, and *Clostridium coskatii*. Additional C1-fixing microorganisms include *Alkalibaculum bacchi, Clostridium thermoaceticum*, and *Clostridium aceticum*.

For instance, Enzien, et al., in United States Published Patent Application 20140206052 A1 disclose methods for producing butanol using C1-fixing homoacetogenic microorganisms and C4-producing butyrogens. See also, Datta, et al., United States Published Patent Application 20140206066 A1. Suitable butyrogens include any microorganisms that contain either or both of the BuCoA AT pathway and BuK pathway and can grow on acetate and ethanol or on acetate and hydrogen as typically found in syngas. Butyrogens known to grow exclusively on ethanol, acetate or syngas include, but are not limited to, *Clostridium kluyveri, Clostridium carboxidivorans*, and *Butyribacterium methylotrophicum*.

Syntrophic C3-producing microorganisms capable of growing on ethanol and/or acetate as their primary carbon source include, but are not limited to, *Pelobacter propionicus, Clostridium* neopropionicum, *Clostridium propionicum. Desulfobulbus propionicus, Syntrophobacter wolinii, Syntrophobacter pfennigii, Syntrophobacter fumaroxidans, Syntrophobacter sulfatireducens, Smithella propionica, Desulfotomaculum thermobenzoicum* subspecies *thermosymbioticum, Pelotomaculum thermopropionicum*, and *Pelotomaculum schinkii*.

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

The aqueous broth is maintained under anaerobic fermentation conditions including a suitable temperature, say, between 25° C. and 65° C., frequently in the range of about 30° to 40° C. for mesophilic microorganism and 50° C. to 60° C. for thermophilic microorganisms. The conditions of fermentation, including the density of microorganisms and aqueous fermentation broth composition are preferably sufficient to achieve the sought conversion efficiency of hydrogen and carbon monoxide. The pH of the aqueous broth is acidic, often between about 4 and 6.0, preferably 4.0 or 4.5 to 5.5. The aqueous fermentation broth typically has a redox potential of less than about −250, preferably between about −250 and −520, millivolts.

The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important.

The bioreactor assembly may comprise one or more bioreactors which may be, with respect to gas flow, in parallel or in series flow. Each bioreactor may be of any suitable design; however, preferably the design and operation provides for a high conversion of carbon monoxide and hydrogen to product alcohol. Fermentation reactors include, but are not limited to, bubble column reactors; jet loop reactors; stirred tank reactors; trickle bed reactors; biofilm reactors including, but not limited to membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

The substrate depleted gas phase egressing from the aqueous fermentation broth will contain a small fraction on a mass basis of the hydrogen and carbon monoxide introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

The bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Impairment of Syngas Supply

The fermentation broth, at the time of the cessation of the syngas flow, will contain alcohol and dissolved syngas as well as other nutrients for the microorganisms. With a planned impairment of syngas supply, preparation for the supply of the formate moiety can be in place, whereas with an unplanned impairment of syngas supply, time may be required to commence the supply of the formate moiety. In either event, preferably within about 2, more preferably within about 0.5, hours of an occurrence of an impairment of syngas supply, the supply of the formate moiety to the fermentation broth is commenced. In some instances, syngas may be supplied to the fermentation broth during the period of impairment, but at a substantially reduced rate.

The fermentation broth may be maintained at substantially the same temperature as that before the impairment of syngas feed in order to facilitate restart of the syngas bioconversion upon the syngas feed being restored. In other instances, it may be desired to reduce the temperature of the fermentation broth in order to reduce metabolic activity and thereby prolong the ability of the methods of this invention to sustain the microorganism population. The cooling may be effected by any suitable means. Since the formate moiety can maintain the viability of the microorganism population at the temperatures used for the fermentation for extended durations of time, it is possible to economically cool the fermentation broth while retaining it in commercial-scale bioreactors. The cooling of the fermentation broth is generally assisted by withdrawing a portion of the broth, subjecting it to indirect heat exchange, and returning it to the bioreactor. As the metabolic activity of the microorganism population is reduced, the heat that they generate is substantially reduced. Hence, the heat exchanger assembly for normal operation of the bioreactor assembly using cooling water is frequently adequate to cool the broth. Where the temperature is reduced during a temporary outage, the reduction is typically in the range of about 5° to 25° C. A temperature range of about 10° C. or 15° C. to 25° C. is often used as such temperatures can be achieved with available cooling water.

The formate moiety is added continuously or intermittently to the fermentation broth in accordance with the method of this invention at a rate and in an amount sufficient to substantially maintain the microorganism population in the aqueous fermentation broth. The rate of addition of the formate moiety can vary or be substantially constant during the duration of the impairment of syngas supply. In some instances, a greater amount of formate moiety is introduced at the commencement of the impairment of the syngas supply such that during the first hour of introduction of the formate moiety, the formate moiety is added at least 120, say, at least 200, and sometimes between about 150 and 500, percent of the average rate of supply. Often, when an initial pulse of formate moiety is used, it is an amount that provides an hourly rate of electron supply of between about 10 and 75, say, 10 and 50, percent of the Prior Electron Supply Rate. The formate moiety may be supplied in any convenient form to the fermentation broth. Typically the formate moiety is supplied as a concentrated aqueous solution. Suitable soluble salts of formate include, but are not limited to, ammonium, alkali metal (preferably one or more of sodium, potassium and cesium), and alkaline earth (preferably calcium) salts. Since the formate moiety is added as a liquid, its distribution throughout the bioreactor is facilitated. This distribution can be assisted in any convenient manner. In some instances, it may be desired to induce mixing of the fermentation broth to aid in distribution of the formate moiety. Stirring or other mechanical mixing or pumping of fermentation broth can be used. For deep tank fermenters, such as bubble column bioreactors, an inert gas, such as nitrogen, can be introduced to replace the syngas feed and thereby enhance mixing. The formate moiety can be supplied at one or more points in the bioreactor. In one embodiment, the formate moiety can be introduced through slot injectors, jet mixers, or the like that are already installed in a bioreactor with or without gas co-feed to facilitate the dispersion.

The rate that the formate moiety is supplied during the period of impairment of the syngas supply is generally sufficient to provide at least about 1 or 2 percent of the electrons from the syngas being consumed prior to the impairment of syngas supply (Prior Electron Supply Rate). The rate of electron consumption form the syngas feed is indicative of the population of viable microorganisms in the broth. A mole of formate anion supplies two moles of electrons. The electrons (in moles) per unit time in the syngas are provided by hydrogen and carbon monoxide and can be calculated as:

$$2[(\text{moles } CO_{in} - \text{moles } CO_{out}) + (\text{moles } H_{2\,in} - \text{moles } H_{2\,out})]$$

where moles $CO_{in}$ are the moles of CO supplied per unit time by the syngas feed, moles $CO_{out}$ are the moles of CO withdrawn from the bioreactor per unit time, moles $H_{2\,in}$ are the moles of $H_2$ supplied per unit time by the syngas feed and moles $H_{2\,out}$ are the moles of $H_2$ withdrawn from the bioreactor prior to the impairment of syngas supply. The upper rate of the supply of formate moiety is usually a factor of cost for the formate moiety versus the benefit in shortening time to resumption of production upon resuming syngas supply.

When adding the formate moiety at a rate equal to only a fraction of the electron moles being supplied by syngas prior to the outage, the viability of the population of microorganisms is maintained while metabolic activity is reduced. Often this reduction is sufficient that it is typically not necessary to continue to add nutrients such as sulfur source, nitrogen source or phosphorus source to the broth during the period of the impairment in syngas supply, especially for brief impairments of syngas supply. Similarly the supply of other nutrients and additives may be reduced or stopped in many instances. In many instances, the population of microorganisms exhibit a metabolic shift such that little, if any, sulfur source is consumed, thus being indicative of an attenuated rate of and often substantially no, reproduction.

It has been found that some reduction in ethanol concentration and increase in acetate anion concentration occurs during the impairment of the syngas supply. Although, upon resumption of syngas supply, the concentrations of both ethanol and acetate typically tend to trend toward those existing prior to the impairment of syngas supply.

Preferably the pH of the broth is maintained between about 4 and 6.0, preferably 4.0 or 4.5 and 5.5. Higher and lower pH conditions tend to adversely affect the population of microorganisms. Since significant amounts of acetic acid are not being produced, maintenance of the desired pH in the broth is facilitated. In some instances, the product alcohol concentration is reduced by less than about 50, preferably less than about 30 or 35, percent after 24 hours of syngas impairment. Often, the mole ratio of product alcohol in the broth that is consumed during the period of the impairment to the formate moiety supplied during that period is less than 1:2, and sometimes between about 0.01:1 to 0.25:1. In some instances, between about 0.1 to 0.4, say, 0.15 to 0.35, mole of gaseous carbon dioxide is evolved from the broth per mole of formate moiety introduced to the broth during the impairment.

The methods of this invention sustain the viability of the population of microorganisms during an impairment in syngas supply. The methods are particularly advantageous for relatively brief durations of impairment, e.g., between about 6 and 30, say, 6 and 12, hours, but due to the metabolic rate attenuation, longer durations of impairment of syngas supply can be addressed even when the temperature of the aqueous fermentation broth is maintained at temperatures used for the syngas bioconversion. It is believed that little, if any, reproduction is occurring. Hence, with extended durations of impairment of syngas supply, a natural loss in the total size of the viable population of microorganisms is expected to occur.

Upon the ability to restore the syngas feed to the aqueous fermentation broth, the transition from the addition of formate moiety to resumption of normal syngas may be effected in any suitable manner. Usually, the rate of syngas feed is increased as the population of microorganisms increases. In most instances, it is preferred to reduce the rate of, or stop, the supply of formate moiety prior to starting or increasing the flow rate of syngas to the aqueous fermentation broth. If needed, the redox potential and pH of the aqueous fermentation broth may be adjusted to enhance the bioconversion of syngas. If the aqueous fermentation broth was cooled to reduce metabolic activity, the temperature of the broth should be increased to the sought temperature either before, during or after the transition from formate moiety to syngas.

Most often, upon resumption of syngas supply, the bioconversion of carbon monoxide recovers more quickly than does the hydrogen conversion. The recovery of carbon monoxide bioconversion is thus a good indicator of the portion of the population of microorganisms that remained viable during the impairment in syngas supply. In preferred aspects of the methods of the invention, recovery of carbon monoxide conversion occurs in less than about 10, preferably in less than about 6, hours after resumption of normal fermentation conditions (i.e., temperature, nutrient and additive concentrations prior to the impairment of syngas flow). In many instances, essentially full recovery of hydrogen uptake is achieved within 20 to 60 hours.

Microorganism Storage and Reactivation

In metabolizing a formate moiety, the microorganisms produce carbon dioxide and reducing equivalents that are used to produce at least one Metabolic Compound. Hydrogen, however, is not evolved from the fermentation broth, and, without wishing to be limited by theory, the reducing equivalents are used by the microorganisms to produce at least one energy storage compound. The energy storage compound can be associated with the microorganism for potential later use. The association can involve the energy storage compound being within the cell, within the cell wall, externally adhering to the cell wall or expressed into the broth. The presence of an energy storage compound thus facilitates maintaining a population of microorganisms under static conditions, i.e., where no substrate is being introduced. Hence, where the microorganisms have developed a reserve of energy storage compound, processing and storage of the microorganisms can occur without undue damage to the population of microorganisms. The processes of this invention take advantage of the buildup of energy storage compound which can be used to sustain the viability of the microorganisms during processing and storage even after the addition of the formate moiety has been stopped.

The microorganisms for storage can be from a portion of the microorganisms in a normally functioning bioreactor or from a bioreactor that has to be shut down due to a loss of syngas, mechanical failure or unavailability of another nutrient. In the instance where the microorganisms for storage are obtained from a normally functioning bioreactor, a portion of the fermentation broth is withdrawn intermittently or continuously from the bioreactor for product recovery. Where the bioreactor has to be shut down, typically fermentation broth is withdrawn to facilitate processing and storage of microorganisms for the bioconversion.

In either event, the formate moiety can be supplied as described above. Where the objective is to develop the supply of energy storage compound, the rate of formate moiety introduction can be greater than that used for a temporary impairment of syngas supply where minimizing cost and reducing metabolic activity is important. Typically the supply of formate moiety is no greater than the rate that the microorganism population can metabolize the formate moiety which is often within the range of about 20 to 100 percent of the electrons being supplied by the syngas on a unit volume of broth prior to the introduction of the formate moiety.

Where the objective is to develop a supply of energy storage compound and the broth is removed from a normally functioning bioreactor for storage, one or more vessels can be used to provide the sought residence time to produce desired amounts of the energy storage compound. Typically, the broth is at substantially the temperature of the bioreactor during the introduction of the formate moiety; however, some cooling may occur with the reduction of metabolic activity by which the generation of heat is reduced. The temperature is often in the range of about 30° C. to 40° C. Especially where greater amounts of energy storage compound are desired, and thus longer periods of treatment with formate moiety are used, the addition of other nutrients can be beneficial. Usually, when supplied, the nutrients are supplied at a rate which is less than 25 or 30 mass percent of that prior to the introduction of the formate moiety.

In preferred embodiments, the fermentation broth containing the microorganisms is continuously or intermittently passed to a solids separating unit operation to provide a solids depleted liquor and a solids rich stream. Any suitable solids separating unit operation may be used. Preferred unit operations are ultrafiltration and those using centrifugal forces such as disk stack centrifuges, decanter centrifuges, tubular and chamber bowl centrifuges, and imperforate basket centrifuges. While often microorganisms are capable of withstanding the forces of the solids separating unit operations, unit operations that provide sought concentrations of solids with less than about 20, preferably less than about 10, percent cell rupturing are preferred. The solids separating unit operation typically provides a solids rich stream that is at least about 5, preferably at least about 20, say, between about 50 to 200 or more, times more concentrated in solids than the fermentation broth. Where an energy storage compound is produced, the association should be of the type that enables a substantial portion of the energy storage compound to be retained with the microorganism concentrate.

At least a portion of the solids rich stream from the solids separating unit operation provides microorganisms for storage.

The cooling of the fermentation broth or, where a separation step is used, the microorganism concentrate, may be effected in any suitable manner using one or both of indirect and direct heat exchange. Direct heat exchange can use one or more of chilled water, ice and dry ice. The temperature is typically lowered to below about 25° C.

Most often, a chilling water stream is used to provide components to enhance the survival and viability of the microorganisms during their storage and reactivation. In addition or alternatively, the chilling water stream may contain one or more of a nitrogen source, sulfur source (especially cysteine), and micronutrients. Various adjuvants to the microorganism concentrate may comprise buffering agents, trace metals, vitamins, salts etc. If desired, the chilling water stream could contain one or more of organic carbon food source and other nutrients. If a chilling water stream is used, it may be desired to subject the broth to a subsequent solids separation unit operation.

The microorganism concentrate is stored until needed without the addition of syngas. Storage includes transport. Preferably the storage is under static conditions. The storage preferably occurs at temperatures below about 25° C., but above the temperatures at which the concentrate freezes, preferably between about 0° C. to 20° C. Often, the storage temperature is in the range of about 0° C. to 25° C., say, 2° C. or 4° C. to 20° C. In some preferred processes of this invention, the microorganism concentrate can be stored for extended durations, e.g., for at least about 3 days, and in some instances in excess of about 30 days, at about 10° C. to 20° C., which reduces costs for cooling. The substantially reduced volume of the microorganism concentrate facilitates its storage in refrigerated facilities.

The pH for the storage may vary widely, and is usually in the range of about 4.0 to 6.0, preferably about 4.0 or 4.5 to 5.5. Buffers may be used to assist in maintaining the sought pH. However, in many instances the reduced metabolic activity of the microorganisms in the microorganism composite is sufficiently low that undue reduction of pH during storage is not observed even in the absence of buffers.

The stored microorganisms can be reactivated in any suitable manner which provides for the microorganisms to be retained in fermentation broth (e.g., by reconstituting a fermentation broth from the concentrate) and increases the temperature of the concentrate to fermentation conditions. A bioreactor can be restarted using any suitable process. Where the start-up of the bioreactor involves increasing the population of the microorganisms and the volume of fermentation broth is increased as the population of the microorganisms increases, a preferred start-up process is disclosed in U.S. Published Patent Application No. 2013/0078693 A1, hereby incorporated by reference in its entirety. The microorganism concentrate may also be used to replenish a depleted population of microorganisms in a reactor. The depleted population in the bioreactor may have occurred due to an operational upset.

Preferably the temperature of the microorganisms are gradually increased prior to being introduced into the bioreactor to avoid any undue stress on the microorganisms. The temperature increase from the temperature of the storage may be effected in any suitable manner including indirect or direct heat exchange.

EXAMPLES

The following examples illustrate, but are not in limitation of, the invention. All parts and percentages of gases and liquids are by volume and of solids are by mass unless otherwise stated or clear from the context.

A stirred, 10 liter, continuous fermenter is used under anaerobic bioconversion conditions with a feed gas comprising about 63.3 volume percent hydrogen; 20.5 volume percent carbon monoxide; 6.8 volume percent carbon dioxide; 8.2 volume percent methane and 1.2 volume percent nitrogen. During steady state operation, the gas feed is supplied at about 280 to 290 milliliters per hour (measured at atmospheric pressure and 25° C.) and a media feed is provided at about 200 milliliters per hour. The media feed is an aqueous solution containing:

| Component | Concentration (g/L) |
|---|---|
| $NH_4Cl$ | 2.500 |
| KCl | 0.524 |
| $KH_2PO_4$ | 0.000 |
| $MgSO_4 * 7H_2O$ | 0.125 |
| $CaCl_2 * 2H_2O$ | 0.075 |
| $H_3PO_4$ | 0.360 |
| $MnSO_4 * H_2O$ | 0.0100 |
| $CoCl_2 * 6H_2O$ | 0.0036 |
| $ZnSO_4 * 7H_2O$ | 0.0020 |
| $NiCl_2 * 6H2O$ | 0.0020 |
| $Na_2MoO_4 * 2H_2O$ | 0.0002 |
| $Na_2SeO_4$ | 0.0010 |
| $Na_2WO_4 * 2H_2O$ | 0.0020 |

-continued

| Component | Concentration (g/L) |
|---|---|
| $FeSO_4 * 7H_2O$ | 0.0486 |
| Thiamine, HCl | 0.00020 |
| Ca - pantothenate | 0.00010 |
| Biotin | 0.00005 |

TABLE 1

| Example | Microorganism |
|---|---|
| 1, 2, 8, 9, 10 and 11 | Clostridium autoethanogenum |
| 3 | Clostridium radsdalei |
| 4, 5, 6, 7 | Clostridium coskatii |

TABLE 2

| Example | Formate moiety | Formate moiety feed rate, mole % of electrons prior to outage | Duration of syngas outage, hrs. | Media feed rate, % of feed rate prior to outage | Sulfur feed during outage | CO uptake recovery | $H_2$ uptake recovery |
|---|---|---|---|---|---|---|---|
| 1 | Sodium salt | 3.5 | 6 | 10 | $Na_2S$, 20 mg/hr | Yes | Yes |
| $2^a$ | Sodium salt | 3.5 | 6 | 10 | $Na_2S$, 20 mg/hr | Yes | Yes |
| 3 | Sodium salt | 5 | 12 | None | None | Yes | Yes |
| 4 | $NH_4^+$ salt | 3.5 | 6 | None | None | Yes | Yes |
| 5 | $NH_4^+$ salt | 3.5 | 24 | None | None | Yes | Yes |
| 6 | $NH_4^+$ salt | 15 | 24 | None | None | Yes | Yes |
| 7 | 2:1 mass ratio Sodium salt Formic acid | 10 | 24 | None | None | Yes | Yes |
| 8 | Sodium salt | 3.5 | 6 | None | None | Yes | Yes |
| 9 | Formic acid | 10 | 6 | None | None | Yes | Yes |
| 10 | Formic acid | 10 | 24 | None | None | Yes | Yes |
| 11 | None | None | 6 | 10 | None | No | No |

$^a$Argon used as sweep gas instead of nitrogen

An aqueous solution of about 60 millimoles of sodium metabisulfite is separately added at a rate of 0.6 milliliters per hour. The fermenter is maintained at about 37° C. at a pH of about 5.0. The stirring rate is approximately 600 revolutions per minute.

In each example, the fermentation, using the microorganism specified in Table 1, is operated to achieve stable, steady-state conditions. The flow of syngas is then stopped. At the time of stoppage of syngas feed, the fermenter is operated in batch mode (no aqueous stream draw from the fermenter), nitrogen gas at about 15 milliliters per minute (atmospheric pressure and 25° C.) is fed to sweep the head space of the fermenter, and the stirring rate is reduced to about 100 rpm. Other conditions during the duration of the cessation of syngas feed are set forth in Table 2. After a predetermined period, the addition of formate moiety is stopped, the nitrogen sweep gas is stopped and the syngas is resumed at a rate that matches the uptake capacity of the microbial population. The stirring is increased to about 600 rpm, and the flow rates of the media feed and metabisulfite feed are resumed to the levels existing prior to the cessation of the syngas feed. Table 2 summarizes the examples.

In all examples, the recovery of CO uptake is more rapid than that for the $H_2$ uptake indicating that a large percentage of the microorganisms survives the outage. The recovery is more rapid at higher formate moiety addition rates than at lower addition rates. After about 6 hours without syngas feed, substantial damage occurs to the microorganism population and no observable recovery occurs.

It is claimed:

1. A method for maintaining viability of at least 25% of a population of microorganisms for the bioconversion of syngas to alcohol in an aqueous fermentation broth in the absence of syngas supply to the fermentation broth, said method comprising continuously or intermittently adding to the fermentation broth during a period of ceased syngas feed a formate moiety comprising at least one of ammonium formate, an alkali metal formate salt, an alkaline earth formate salt, and formic acid, wherein the viability of at least 25% of the population of microorganisms is maintained.

2. The method of claim 1, for maintaining viability of at least 25% of a population of microorganisms having the Wood-Ljungdahl pathway for the bioconversion of syngas to alcohol in an aqueous fermentation broth in the absence of syngas supply to the fermentation broth, said method comprising continuously or intermittently adding to the fermentation broth during a period of ceased syngas feed a formate moiety comprising at least one of ammonium formate, an alkali metal formate salt, an alkaline earth formate salt, and formic acid at a rate sufficient to maintain the viability of at least 25% of the microorganism population.

3. The method of claim 1, wherein the formate moiety comprises at least one of ammonium formate, an alkali metal formate salt, or an alkaline earth formate salt.

4. The method of claim 1, wherein the addition of formate moiety to the fermentation broth is sufficient to provide at least about 2 mole percent of the electrons that were provided to the fermentation broth by the syngas prior to the impairment of syngas supply.

5. The method of claim 4, wherein the rate of addition of formate moiety to the fermentation broth provides between about 2 and 15 mole percent of the electrons being provided to the fermentation broth prior to the impairment of syngas supply.

6. The method of claim 1, wherein the formate moiety comprises at least one of sodium formate and ammonium formate.

7. The method of claim 1, wherein acid is introduced intermittently or continuously to maintain the pH within the range of about 4.5 to 5.5.

8. The method of claim 1, wherein the formate moiety is added continuously.

9. The method of claim 1, wherein carbon monoxide conversion recovers in less than about 6 hours after resumption of syngas supply at the temperature and nutrient and additive concentrations prior to cessation of syngas feed.

10. The method of claim 1, wherein the broth is cooled to between 10° C. and 25° C. during the period of ceased syngas feed.

11. The method of claim 1, wherein the aqueous fermentation broth is contained in a commercial-scale bioreactor.

12. The method of claim 1 wherein:
the addition of formate moiety to the fermentation broth is sufficient to provide at least about 2 mole percent of the electrons that were provided to the fermentation broth by the syngas prior to the cessation of syngas supply;
the rate of addition of formate moiety to the fermentation broth provides between about 2 and 15 mole percent of the electrons being provided to the fermentation broth prior to the cessation of syngas supply;
acid is introduced intermittently or continuously to maintain the pH within the range of about 4.5 to 5.5; and
the formate moiety is added continuously.

13. A process for the storage and reactivation of microorganisms for the bioconversion of syngas to alcohol comprising:
a. continuously or intermittently introducing into a fermentation broth containing said microorganisms at least one formate moiety of the group consisting of soluble formate salt and formic acid under fermentation conditions to produce at least one energy storage compound in the absence of syngas;
b. cooling the microorganisms to a temperature below about 25° C.;
c. storing said cooled microorganisms at a temperature below about 25° C.; and
d. reactivating the stored microorganisms by warming to a temperature between about 30° C. and 40° C. in the presence of the at least one energy storage compound and subjecting the microorganisms to syngas fermentation conditions including supplying syngas.

14. The process of claim 13, wherein the fermentation broth of step (a) is separated to provide a solids depleted liquor phase and a microorganism concentrate of said microorganisms having said at least one energy storage compound associated therewith.

15. The process of claim 13, wherein step (a) is conducted for between 1 and 24 hours.

16. The process of claim 13, wherein formate moiety is introduced continuously or intermittently during step (d) until the microorganisms are at a desired temperature for syngas conversion.

17. The process of claim 13, wherein the storage of step (c) is static.

18. The process of claim 13, which is a process for the bioconversion of syngas to alcohol, said process comprising, prior to step (a), the steps of:
introducing syngas into a fermentation broth comprising a population of microorganisms, bio-converting the syngas to alcohol, and
terminating the flow of syngas into the fermentation broth.

* * * * *